US006277822B1

(12) United States Patent
Kolbe et al.

(10) Patent No.: US 6,277,822 B1
(45) Date of Patent: Aug. 21, 2001

(54) FAMILY OF PEPTIDES KNOWN AS XENOXINS

(75) Inventors: Hanno V. J. Kolbe; Ulla B. Rasmussen, both of Geispolsheim (FR); Günther Kreil, Anif (AT); Tilman Achstetter, Oberkirch (DE)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/498,346

(22) Filed: Feb. 4, 2000

Related U.S. Application Data

(62) Division of application No. 08/578,674, filed as application No. PCT/FR94/00780 on Jun. 28, 1994.

(30) Foreign Application Priority Data

Jun. 29, 1993 (EP) .................................................. 9307901
Jan. 11, 1994 (EP) .................................................. 9400202
Jan. 11, 1994 (EP) .................................................. 94400062

(51) Int. Cl.[7] ............................ A61K 38/00; C07K 1/00; C07K 14/00; C12P 21/06

(52) U.S. Cl. .................... 514/12; 424/184.1; 424/185.1; 530/300; 530/350; 435/69.1

(58) Field of Search .................................. 435/69.1–417; 424/184.1, 185.1; 530/300, 380; 514/12

(56) References Cited

U.S. PATENT DOCUMENTS 5,232,911 8/1993 Vidal .

FOREIGN PATENT DOCUMENTS 0 261 534 A3 3/1988 (EP) .
0 349 451 A1 1/1990 (EP) .
0 607 080 A1 7/1994 (EP) .
WO 90/13646 11/1990 (WO) .

OTHER PUBLICATIONS

Kolbe et al., *Journal of Biological Chemistry*, vol. 268, No. 22, pp 16458–16464, Aug. 5, 1993.*

Brake et al., Proceedings of the National Academy of Sciences of USA, 81: 4642–4646 (1984).

Reichart et al., Invertebrate Reproduction and Development, 21(1): 15–24 (1992).

Charlier et al., Gene, 77: 341–348 (1989).

Kolbe et al., Journal of Biological Chemistry, 268(22): 16458–16464 (1993).

Dimarcq et al., EMBO Journal, 9(8): 2507–2515 (1990).

Inoue et al., FEBS Letters, 218(1): 17–21 (1987).

* cited by examiner

*Primary Examiner*—Avis M. Davenport
(74) *Attorney, Agent, or Firm*—Burns, Doane, Swecker & Mathis, L.L.P.

(57) ABSTRACT

Peptide family designated as xenonins, wherein the representative members can be isolated from the substance secreted from the skin of *Xenopus laevis,* and having precious pharmaceutical properties.

21 Claims, 4 Drawing Sheets

```
Xénoxine[a]      LKCVNLQANGIKMTQECAKEDTKCLTLRSLKKT-LKF-----CASGRTCTTMKIMSLPGEQITCCEGNMCNA
Cytotoxine[b]    LKCHNTQLPFIYKT--CPEGKNLCFKA-TLKKFPLKIPIKRGCAD--NCPKNSALL----KYVCCSTDKCN
Neurotoxine[c]   RRCFNQQSSQPKTTKSCPPGENSCYNKQWRDHRGSI--TERGCG----CPKVK----PGIKLRCCESEDCNN
```

FIGURE 3A

| | | C | | C | | C | | C | | C | | CC | | C | |
|---|---|---|---|---|---|---|---|---|---|---|---|---|---|---|---|
| XENOXINES | 2 | | 13 | | 6 | | 12 | | 5 | | 14 | | 4 | | 2 |
| CYTOTOXINES | 2 | | 10-11 | | 6 | | 15-17 | | 3 | | 10 | | 4 | | 1-2 |
| NEUROTOXINES | 2 | | 12-13 | | 4-6 | | 15-16 | | 1 | | 8-11 | | 4 | | 2 |

FIGURE 3B

```
                  |             |      |            |      |                ||   |
Xénoxine-1      LKCVNLQANGIKMTQECAKEDTKCLTLRSLKKTLKFCASGRT-CTTMKIMSLPGEQITCCEGNMCNA
                                                    C    RT C   K  S P      CCEGNMCN
Récepteur
humain         VEPCYGDKDKRRHCFATWKNISGSIEIVKQGCWLDDINCY-DRTDCVEKK-DS-PEVYFCCCEGNMCNEKF
d'activine        |         |                 |      |      |                 |||   |
```

FIGURE 4

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
(A) LENGTH: 462 base pairs
(B) TYPE: nucleic acid
(C) STRANDEDNESS: single
(D) TOPOLOGY: linear -continued (ii) MOLECULE TYPE: cDNA to mRNA (ix) FEATURE:
(A) NAME/KEY: CDS
(B) LOCATION: 39..290
(D) OTHER INFORMATION: /codon_start= 39 /product= "prexenoxin-1" /note= "the signal peptide comprises the first eighteen amino acid residues"

(xi) SEQUENCE DESCRIPTION: SEQ ID NO:1:

```
AAGATGTGCT GTGATTGGTT GAAAGCTTGA GCCACACA ATG CGT TAC GCC ATC         53
                                          Met Arg Tyr Ala Ile
                                            1               5

GTC TTC TTT CTC GTT TGT GTC ATT ACT CTT GGA GAA GCA CTG AAA TGT      101
Val Phe Phe Leu Val Cys Val Ile Thr Leu Gly Glu Ala Leu Lys Cys
                 10                  15                  20

GTG AAT TTA CAA GCG AAT GGA ATA AAG ATG ACA CAA GAG TGT GCA AAG      149
Val Asn Leu Gln Ala Asn Gly Ile Lys Met Thr Gln Glu Cys Ala Lys
             25                  30                  35

GAG GAT ACC AAA TGC TTA ACA TTA AGA TCA TTA AAA AAA ACT TTA AAG      197
Glu Asp Thr Lys Cys Leu Thr Leu Arg Ser Leu Lys Lys Thr Leu Lys
         40                  45                  50

TTT TGT GCC TCT GGT CGA ACA TGT ACG ACT ATG AAA ATA ATG TCT TTG      245
Phe Cys Ala Ser Gly Arg Thr Cys Thr Thr Met Lys Ile Met Ser Leu
     55                  60                  65

CCT GGG GAA CAG ATT ACA TGC TGT GAA GGA AAC ATG TGC AAT GCT          290
Pro Gly Glu Gln Ile Thr Cys Cys Glu Gly Asn Met Cys Asn Ala
 70                  75                  80

TGAGATGATT CTTCCAATGG AGGTTGCCGG GATTTTCTCT TCTCACATGA AGCAATGGCC    350

CTACCAAAAC ATTTGTCCTC TCCTCTCTCC TCTTTTCCCT TCTGTCCACT CTCCTATAGA    410

TACTAGGGTG TAGCTTGATT CCTAATATCC ATTAAATAAA GCACTCAACT GC            462
```

(2) INFORMATION FOR SEQ ID NO:2:

(i) SEQUENCE CHARACTERISTICS:
(A) LENGTH: 84 amino acids
(B) TYPE: amino acid
(D) TOPOLOGY: linear (ii) MOLECULE TYPE: protein (xi) SEQUENCE DESCRIPTION: SEQ ID NO:2:

```
Met Arg Tyr Ala Ile Val Phe Phe Leu Val Cys Val Ile Thr Leu Gly
  1               5                  10                  15

Glu Ala Leu Lys Cys Val Asn Leu Gln Ala Asn Gly Ile Lys Met Thr
             20                  25                  30

Gln Glu Cys Ala Lys Glu Asp Thr Lys Cys Leu Thr Leu Arg Ser Leu
         35                  40                  45

Lys Lys Thr Leu Lys Phe Cys Ala Ser Gly Arg Thr Cys Thr Thr Met
     50                  55                  60

Lys Ile Met Ser Leu Pro Gly Glu Gln Ile Thr Cys Cys Glu Gly Asn
 65                  70                  75                  80

Met Cys Asn Ala
```

(2) INFORMATION FOR SEQ ID NO:3:

(i) SEQUENCE CHARACTERISTICS:
(A) LENGTH: 66 amino acids
(B) TYPE: amino acid
(C) STRANDEDNESS: single
(D) TOPOLOGY: linear -continued (ii) MOLECULE TYPE: peptide (xi) SEQUENCE DESCRIPTION: SEQ ID NO:3:

```
Leu Lys Cys Val Asn Leu Gln Ala Asn Gly Ile Lys Met Thr Gln Glu
1               5                   10                  15

Cys Ala Lys Glu Asp Thr Lys Cys Leu Thr Leu Arg Ser Leu Lys Lys
            20                  25                  30

Thr Leu Lys Phe Cys Ala Ser Gly Arg Thr Cys Thr Thr Met Lys Ile
        35                  40                  45

Met Ser Leu Pro Gly Glu Gln Ile Thr Cys Cys Glu Gly Asn Met Cys
    50                  55                  60

Asn Ala
65
```

(2) INFORMATION FOR SEQ ID NO:4:

(i) SEQUENCE CHARACTERISTICS:
(A) LENGTH: 66 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

```
Leu Lys Cys Val Asn Leu Gln Ala Asn Gly Ile Lys Met Thr Gln Glu
1               5                   10                  15

Cys Ala Lys Glu Asp Asn Lys Cys Leu Thr Leu Arg Ser Leu Lys Lys
            20                  25                  30

Thr Leu Lys Phe Cys Ala Ser Asp Arg Ile Cys Lys Thr Met Lys Ile
        35                  40                  45

Met Ser Leu Pro Gly Glu Lys Ile Thr Cys Cys Glu Gly Asn Met Cys
    50                  55                  60

Asn Ala
65
```

(2) INFORMATION FOR SEQ ID NO:5:

(i) SEQUENCE CHARACTERISTICS:
(A) LENGTH: 66 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Leu Lys Cys Val Asn Leu Gln Ala Asn Gly Val Lys Met Thr Gln Glu
1               5                   10                  15

Cys Ala Lys Glu Asp Thr Lys Cys Leu Thr Leu Arg Ser Leu Lys Lys
            20                  25                  30

Thr Leu Lys Phe Cys Ala Ser Asp Arg Ile Cys Lys Thr Met Lys Ile
        35                  40                  45

Ala Ser Leu Pro Gly Glu Gln Ile Thr Cys Cys Glu Gly Asn Met Cys
    50                  55                  60

Asn Ala
65
```

(2) INFORMATION FOR SEQ ID NO:6:

-continued (i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..37
(D) OTHER INFORMATION: /note= "analysed portion of xenoxine-1, alkylated"

(xi) SEQUENCE DESCRIPTION: SEQ ID NO:6:

```
Leu Lys Cys Val Asn Leu Gln Ala Asn Gly Ile Lys Met Thr Gln Glu
1               5                   10                  15

Cys Ala Lys Glu Asp Thr Lys Cys Leu Thr Leu Arg Ser Leu Lys Lys
            20                  25                  30

Thr Leu Lys Phe Cys
        35
```

(2) INFORMATION FOR SEQ ID NO:7:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..43
(D) OTHER INFORMATION: /note= "xenoxin-1, alkylated, fragment CNBR1(1)"

(xi) SEQUENCE DESCRIPTION: SEQ ID NO:7:

```
Leu Lys Cys Val Asn Leu Gln Ala Asn Gly Ile Lys Xaa Xaa Gln Glu
1               5                   10                  15

Cys Ala Lys Glu Asp Thr Lys Cys Leu Thr Leu Arg Ser Leu Lys Lys
            20                  25                  30

Thr Leu Lys Phe Cys Ala Xaa Xaa Xaa Thr Cys
        35                  40
```

(2) INFORMATION FOR SEQ ID NO:8:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..31
(D) OTHER INFORMATION: /note= "xenoxin-1, alkylated, fragment CNBR1(2)"

(xi) SEQUENCE DESCRIPTION: SEQ ID NO:8:

```
Thr Gln Glu Cys Ala Lys Glu Asp Thr Lys Cys Leu Thr Xaa Arg Ser
1               5                   10                  15

Leu Lys Lys Thr Leu Lys Phe Cys Ala Xaa Gly Arg Thr Cys Thr
            20                  25                  30
```

-continued (2) INFORMATION FOR SEQ ID NO:9:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..8
(D) OTHER INFORMATION: /note= "xenoxin-1, alkylated, fragment CL1(1)"

(xi) SEQUENCE DESCRIPTION: SEQ ID NO:9:

Leu Lys Cys Val Asn Leu Gln Ala
1 5

(2) INFORMATION FOR SEQ ID NO:10:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..12
(D) OTHER INFORMATION: /note= "xenoxin-1, alkylated, fragment CL1(2)"

(xi) SEQUENCE DESCRIPTION: SEQ ID NO:10:

Ser Leu Lys Lys Thr Leu Lys Phe Cys Ala Ser Gly
1 5 10

(2) INFORMATION FOR SEQ ID NO:11:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..6
(D) OTHER INFORMATION: /note= "xenoxin 1, alkylated, fragment T1(1)"

(xi) SEQUENCE DESCRIPTION: SEQ ID NO:11:

Thr Xaa Thr Thr Met Lys
1 5

(2) INFORMATION FOR SEQ ID NO:12:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..19

-continued (D) OTHER INFORMATION: /note= "xenoxin-1, fragment T1(2)"

(xi) SEQUENCE DESCRIPTION: SEQ ID NO:12:

Ile Met Ser Leu Pro Gly Glu Gln Ile Thr Xaa Xaa Glu Gly Asn Met
1 5 10 15

Xaa Asn Ala (2) INFORMATION FOR SEQ ID NO:13:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..13
(D) OTHER INFORMATION: /note= "xenoxin-1, alkylated, fragment CNBR2(1)"

(xi) SEQUENCE DESCRIPTION: SEQ ID NO:13:

Ser Leu Pro Gly Glu Gln Ile Thr Cys Cys Glu Gly Asn
1 5 10

(2) INFORMATION FOR SEQ ID NO:14:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..16
(D) OTHER INFORMATION: /note= "xenoxin-1, alkylated, fragment CNBR2(2)"

(xi) SEQUENCE DESCRIPTION: SEQ ID NO:14:

Lys Ile Met Ser Leu Pro Gly Glu Gln Ile Thr Cys Cys Glu Gly Asn
1 5 10 15

(2) INFORMATION FOR SEQ ID NO:15:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..18
(D) OTHER INFORMATION: /note= "xenoxin-1, alkylated, fragment CL2"

(xi) SEQUENCE DESCRIPTION: SEQ ID NO:15:

Ile Met Ser Leu Pro Gly Glu Gln Ile Thr Cys Cys Glu Gly Asn Met
1 5 10 15

Cys Asn (2) INFORMATION FOR SEQ ID NO:16:

-continued (i) SEQUENCE CHARACTERISTICS:
(A) LENGTH: 56 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..56
(D) OTHER INFORMATION: /note= "analysed portion of xenoxin-2, alkylated"

(xi) SEQUENCE DESCRIPTION: SEQ ID NO:16:

```
Leu Lys Cys Val Asn Leu Gln Ala Asn Gly Ile Lys Met Thr Gln Glu
1               5                   10                  15

Cys Ala Lys Glu Asp Asn Lys Cys Leu Thr Leu Arg Ser Leu Lys Lys
            20                  25                  30

Thr Leu Lys Phe Cys Ala Xaa Asp Arg Ile Cys Lys Thr Met Lys Ile
        35                  40                  45

Met Ser Leu Pro Gly Glu Xaa Ile
    50                  55
```

(2) INFORMATION FOR SEQ ID NO:17:

(i) SEQUENCE CHARACTERISTICS:
(A) LENGTH: 47 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..47
(D) OTHER INFORMATION: /note= "analysed portion of xenoxin-2"

(xi) SEQUENCE DESCRIPTION: SEQ ID NO:17:

```
Leu Lys Xaa Val Asn Leu Gln Ala Asn Gly Ile Lys Met Thr Gln Glu
1               5                   10                  15

Xaa Ala Lys Glu Asp Asn Lys Xaa Leu Thr Leu Arg Ser Leu Lys Lys
            20                  25                  30

Thr Leu Lys Phe Cys Ala Ser Asp Xaa Ile Xaa Lys Thr Met Lys
        35                  40                  45
```

(2) INFORMATION FOR SEQ ID NO:18:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..11
(D) OTHER INFORMATION: /note= "xenoxin-2, alkylated, fragment CL3"

(xi) SEQUENCE DESCRIPTION: SEQ ID NO:18:

```
Ile Thr Cys Cys Glu Gly Asn Met Cys Asn Ala
1               5                   10
```

-continued (2) INFORMATION FOR SEQ ID NO:19:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..8
(D) OTHER INFORMATION: /note= "xenoxin-2, fragment T3"

(xi) SEQUENCE DESCRIPTION: SEQ ID NO:19:

```
Ile Met Ser Leu Pro Gly Glu Lys
1               5
```

(2) INFORMATION FOR SEQ ID NO:20:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..20
(D) OTHER INFORMATION: /note= "analysed portion of xenoxin-3, alkylated (1)"

(xi) SEQUENCE DESCRIPTION: SEQ ID NO:20:

```
Leu Xaa Cys Val Asn Leu Gln Ala Asn Gly Xaa Lys Met Xaa Gln Glu
1               5                   10                  15

Cys Xaa Lys Glu
            20
```

(2) INFORMATION FOR SEQ ID NO:21:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..20
(D) OTHER INFORMATION: /note= "analysed portion of xenoxin-3, alkylated (2)"

(xi) SEQUENCE DESCRIPTION: SEQ ID NO:21:

```
Lys Cys Val Asn Leu Gln Ala Asn Gly Val Lys Met Thr Gln Glu Cys
1               5                   10                  15

Ala Lys Glu Asp
            20
```

(2) INFORMATION FOR SEQ ID NO:22:

(i) SEQUENCE CHARACTERISTICS:
(A) LENGTH: 20 amino acids
(B) TYPE: amino acid
(C) STRANDEDNESS: single
(D) TOPOLOGY: linear -continued (ii) MOLECULE TYPE: peptide (ix) FEATURE:
(A) NAME/KEY: Peptide
(B) LOCATION: 1..20
(D) OTHER INFORMATION: /note= "analysed portion of xenoxin-3, alkylated (3)"

(xi) SEQUENCE DESCRIPTION: SEQ ID NO:22:

```
Cys Val Asn Leu Gln Ala Asn Gly Val Lys Met Thr Gln Glu Cys Ala
1               5                   10                  15

Lys Glu Asp Thr
            20
```

(2) INFORMATION FOR SEQ ID NO:23:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..6
(D) OTHER INFORMATION: /note= "xenoxin-3, alkylated fragment T4"

(xi) SEQUENCE DESCRIPTION: SEQ ID NO:23:

```
Phe Cys Ala Ser Asp Arg
1               5
```

(2) INFORMATION FOR SEQ ID NO:24:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..19
(D) OTHER INFORMATION: /note= "xenoxin-3, alkylated, fragment T5"

(xi) SEQUENCE DESCRIPTION: SEQ ID NO:24:

```
Ile Ala Ser Leu Pro Gly Glu Gln Ile Thr Cys Cys Glu Gly Asn Met
1               5                   10                  15

Cys Asn Ala
```

(2) INFORMATION FOR SEQ ID NO:25:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..19
(D) OTHER INFORMATION: /note= "xenoxin-3, alkylated, fragment T6"

-continued (xi) SEQUENCE DESCRIPTION: SEQ ID NO:25:

```
Ile Ala Ser Leu Pro Gly Glu Gln Ile Thr Xaa Xaa Glu Gly Asn Met
1               5                   10                  15

Xaa Asn Ala
```

(2) INFORMATION FOR SEQ ID NO:26:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: modified_base
(B) LOCATION: 20
(D) OTHER INFORMATION: /mod_base= i (ix) FEATURE:
(A) NAME/KEY: misc_feature
(B) LOCATION: 1..28
(D) OTHER INFORMATION: /note= "oligonucleotide OTG3278"

(xi) SEQUENCE DESCRIPTION: SEQ ID NO:26:

ATGTCGACCA RGARTGYGCN AARGARGA 28

(2) INFORMATION FOR SEQ ID NO:27:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: modified_base
(B) LOCATION: 17
(D) OTHER INFORMATION: /mod_base= i (ix) FEATURE:
(A) NAME/KEY: misc_feature
(B) LOCATION: 1..28
(D) OTHER INFORMATION: /note= "oligonucleotide OTG3279"

(xi) SEQUENCE DESCRIPTION: SEQ ID NO:27:

ATAAGCTTCA CATRTTNCCY TCRCARCA 28

(2) INFORMATION FOR SEQ ID NO:28:

(i) SEQUENCE CHARACTERISTICS:
(A) LENGTH: 149 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: misc_feature
(B) LOCATION: 1..149
(D) OTHER INFORMATION: /product= "PCR1" /note= "PCT cDNA fragment used for the screening described in Example 2.5"

(xi) SEQUENCE DESCRIPTION: SEQ ID NO:28:

-continued

| | |
|---|---|
| CAGGAGTGTG CGAAGGAGGA TAACAAATGC TTAACATTAA GATCGTTAAA AAAAACTTTA | 60 |
| AAGTTTTGTG CCTCTGATCG AATATGTAAG ACTATGAAAA TAATGTCTCT GCCTGGGGAA | 120 |
| AAGATTACAT GCTGCGAAGG CAACATGTG | 149 |

FAMILY OF PEPTIDES KNOWN AS XENOXINS

This application is a divisional, of application Ser. No. 08/578,674, filed Dec. 28, 1995, which is a 371 of PCT/FR94/00780, filed Jun. 28, 1994.

The present invention relates to a family of peptides known as xenoxins, to the members of the peptide family as well as to methods for preparing them and to the corresponding DNA sequences. It also relates to pharmaceutical compositions containing said xenoxins as well as to diagnostic kits containing them or containing anti-xenoxin antibodies.

A large number of peptides with various biological functions have already been isolated from the skin or skin secretions of amphibia (V. Erspamer and P. Melchiorri, Neuroendocrine Perspectives, E. E. Müller and McLeod, Eds., (Elsevier Science Publishers B.V.) 2, (1983), p 37; C. L. Bevins et al.; Ann. Rev. Biochem. 59; (1990); p 395). From the outset, it was found that several of these peptides were very similar or even identical to hormones and neutrotransmitters of mammals (V. Erspamer et al., Trends Pharmacol. Sci. 1, (1980), p 391).

Thus, frog's skin and skin secretions is [sic] held to be a source of peptides with advantageous pharmacological or antibiotic properties. More especially, the skin of *Xenopus laevis*, a frog of African origin, contains large concentrations of various peptides.

The biological role which may be performed by these peptides which are to be found in the matter secreted by the glands and skin of *Xenopus laevis* is only partially known. On the one hand, the secretions might have a protective function since the secreted matter would appear to be harmful to predators. On the other hand, the secreted matter contains peptides which limit the growth of bacteria and fungi, and which might hence behave as antibiotics on the wet skin of the frog or combat infections during wound healing.

These antibiotic peptides contain, in general, between 21 and 26 amino acids, are basic and are free from tyrosine. The identity of the amino acid sequences of the different antibiotic peptides is often very limited. In contrast, these peptides have their amphipathic alpha-helical conformation in common. In respect of the signal sequences of approximately 20 amino acids, the identity of the amino acid sequences is only 55%. However, conserved segments are to be found, common to the signal sequences of the different antibiotic peptides. Furthermore, they all share an N-terminal Arg-Xaa-Val-Arg sequence which is considered to the site of action of a common maturation enzyme.

As other examples of peptides isolated and characterized in *Xenopus laevis,* there may be mentioned caerulein, a member of the cholecystokinin/gastrin peptide family (Anastasi et al., Brit. J. Pharmacol. 38, (1970), p 221); spasmolysin I and II (W. Hoffmann, J. Biol. Chem. 263 (16), (1988), p 7686); thyrotropin releasing peptide (K. Richter et al., EMBO J. 3(3), (1984), p 617) and xenopsin (K. Araki et al., Chem. Pharmacol. Bull. 21 (12), (1973), p 2801). Most of these peptides are members of a peptide family which contains, inter alia, analogous peptides of mammalian origin. Bombesin and kassinin, for example, have been used as reference to identify gastrin releasing peptide and substance K, respectively, in mammals (C. L. Bevins et al, see above). In point of fact, the matter secreted by frog's skin contains peptides in copious amounts, while the analogous peptide in mammals is often present only in small amounts. Thus, the frog peptides lend themselves to the identification of useful mammalian peptides.

The present invention relates to a new family of peptides which have been named xenoxins and which possess valuable pharmaceutical properties, and especially the property of influencing the functioning of transmembrane ion channels while not displaying neurotoxic activity. Furthermore, it is thought that these peptides would have the advantageous property of abolishing the effects of activin.

More especially, the present invention relates to a xenoxin which is characterized in that it comprises an amino acid sequence which:

a. contains at least 8 cysteines (Cys) which are linked through 4 disulfide bridges according to the arrangement $Cys^1$ with $Cys^3$, $Cys^2$ with $Cys^4$, $Cys^5$ with $Cys^6$ and $Cys^7$ with $Cys^8$;

b. contains 0 to 3 amino acids on the N-terminal side of $Cys^1$, 9 to 14 amino acids between $Cys^1$ and $Cys^2$, 3 to 7 amino acids between $Cys^2$ and $Cys^3$, 11 to 18 amino acids between $Cys^3$ and $Cys^4$, 1 to 6 amino acids between $Cys^4$ and $Cys^4$, 7 to 15 amino acids between $Cys^5$ and $Cys^6$, no amino acid between $Cys^6$ and $Cys^7$, 3 to 5 amino acids between $Cys^7$ and $Cys^8$ and 0 to 10 amino acids on the C-terminal side of $Cys^8$; and C. displays an identity of amino acids, after alignment, of at least 40% with the amino acid sequence identified under the number SEQ ID NO: 3, or a fragment derived from this sequence.

The term xenoxin refers to a small basic protein displaying the features described.

In the context of the present invention, the number appearing as index against a cysteine residue indicates its position relative to the other cysteines in said xenoxin in the N- to C-terminal direction. Thus $Cys^1$ refers to the first cysteine appearing in a xenoxin according to the invention on the N-terminal side.

The present invention also relates to the intermediate peptides which have not yet adopted their folded conformation but which contain at least 8 cysteines capable of linking to one another through 4 disulphide bridges according to the arrangement $Cys^1$ with $Cys^3$, $Cys^2$ with $Cys^4$, $Cys^5$ with $Cys^6$ and $Cys^7$ with $Cys^8$.

Thus, the present invention relates to a basic peptide which is characterized in that it comprises an amino acid sequence which:

a. contains at least 8 cysteines which, when the peptide adopts its folded conformation, are linked through 4 disulfide bridges according to the arrangement $Cys^1$ with $Cys^3$, $Cys^2$ with $Cys^4$, $Cys^5$ with $Cys^6$ and $Cys^7$ with $Cys^8$;

b. contains 0 to 3 amino acids on the N-terminal side of $Cys^1$, 9 to 14 amino acids between $Cys^1$ and $Cys^2$, 3 to 7 amino acids between $Cys^2$ and $Cys^3$, 11 to 18 amino acids between $Cys^3$ and $Cys^4$, 1 to 6 amino acids between $Cys^4$ and $Cys^5$, 7 to 15 amino acids between $Cys^5$ and $Cys^6$, no amino acid between $Cys^6$ and $Cys^7$, 3 to 5 amino acids between $Cys^7$ and $Cys^8$ and 0 to 10 amino acids on the C-terminal side of $Cys^8$; and c. displays an identity of amino acids, after alignment, of at least 40% with the amino acid sequence identified under the number SEQ ID NO: 3, or fragment derived from this sequence.

Preferred peptides of the present invention contain two amino acids on the N-terminal side of $Cys^1$, 10 to 13 amino acids between $Cys^1$ and $Cys^2$, 4 to 6 amino acids between $Cys^2$ and $Cys^3$, 12 to 17 amino acids between $Cys^3$ and $Cys^4$, 1 to 5 amino acids between $Cys^4$ and $Cys^5$, 8 to 14 amino acids between $Cys^5$ and $Cys^6$, no amino acid between $Cys^6$ and $Cys^7$, 4 amino acids between $Cys^7$ and $Cys^8$ and 2 amino acids on the C-terminal side of $Cys^8$.

Other peptides, also preferred, of the present invention display an identity of amino acids of at least 50%, as a special preference of at least 60% and advantageously of at least 70%, with the amino acid sequence identified under the number SEQ ID NO: 3.

Especially preferred peptides according to the invention are the xenoxins which are characterized in that they comprise an amino acid sequence which:

a. contains at least 8 cysteines which are linked through 4 disulfide bridges according to the arrangement $Cys^1$ with $Cys^3$, $Cys^2$ with $Cys^4$, $Cys^5$ with $Cys^6$ and $Cys^7$ with $Cys^8$;

b. contains 0 to 3 amino acids on the N-terminal side of $Cys^1$, 13 amino acids between $Cys^1$ and $Cys^2$, 6 amino acids between $Cys^2$ and $Cys^3$, 12 amino acids between $Cys^3$ and $Cys^4$, 5 amino acids between $Cys^4$ and $Cys^5$, 14 amino acids between $Cys^5$ and $Cys^6$, no amino acid between $Cys^6$ and $Cys^7$, 4 amino acids between $Cys^7$ and $Cys^8$ and 0 to 10 amino acids on the C-terminal side of $Cys^8$; and c. displays an identity of amino acids, after alignment, of at least 80%, and preferably 90%, with the amino acid sequence identified under the number SEQ ID NO: 3.

The peptides according to the invention advantageously contain from 42 to 86 amino acids, preferably from 51 to 75 amino acids and as a special preference from 62 to 75 amino acids.

The present invention also relates to peptides of 66 amino acids which display an identity of amino acids, after alignment, of at least 80%, preferably of at least 90% and as a special preference of at least 95%, with the amino acid sequence as identified under the number SEQ ID NO:3.

As examples of especially preferred peptides, the peptides xenoxin-1 as identified under the number SEQ ID NO: 3, as well as xenoxin-2 according to SEQ ID NO: 4 and xenoxin-3 according to SEQ ID NO: 5, may be mentioned.

To determine the degree of identity of amino acids, the cysteines are aligned in such a way that they occur in an identical position with the cysteines of the amino acid sequence as presented under SEQ ID NO: 3, and the minimum number of insertions or deletions is introduced in order to maximize the alignment of the sequences. The identical amino acids which occur at an identical position, including the cysteines, are then identified. The identity of amino acids is expressed as a percentage and calculated according to the following formula (1):

$$\frac{n}{66+p}\times 100 \qquad (1)$$

in which n is the number of identical amino acids, 66 is the number of amino acids of the sequence identified under the number SEQ ID NO: 3, p is the number of insertions or deletions introduced.

The peptides according to the invention can be in the form of their addition salts with pharmaceutically acceptable, nontoxic acids. As examples of pharmaceutically acceptable acids, inorganic acids such as hydrochloric, sulfuric, phosphoric, and the like, acids, and organic acids such as sulfonic and carboxylic acids, for instance acetic, lactic, palmitic, stearic, maleic, tartaric, ascorbic, citric, and the like, acids, may be mentioned.

The peptides according to the invention may also be in the form of their additional salts with a base, since they contain free carboxyl groups. As examples of pharmaceutically acceptable salts, the sodium, potassium, calcium or magnesium salts and the quaternary ammonium derivatives may be mentioned.

Since the peptides of the invention contain both free carboxyl and amine groups, they can be in the form of their internal salts or in the combined form of addition salts and internal salts.

A family of xenoxins according to the invention comprises peptides which originate from different species of amphibia or mammals. As an example of amphibia, there may be mentioned the species which belong to the super order Salienta, anurans such as frogs,toads, tree frogs, and the like; or to the order Caudata, urodeles such as salamanders, newts, and the like; or alternatively to the order Gymnophiona, apodals such as eels, morays, and the like. It is also possible to obtain mammalian xenoxins, in particular from mice, pigs or humans.

The xenoxins according to the invention have pharmaceutical properties in common in mammals, based, in particular, on their interactions with the functioning of transmembrane ion channels and their interaction with activin.

The identity of amino acids of the different xenoxins can vary on account of interspecies or allelic divergences. More often than not the variations comprise conservative substitutions which enable the skeletal conformation of the peptide to be preserved. Thus, as a preference, in the xenoxins according to the invention, a substitution at a homologous position, compared with the sequence identified under SEQ ID NO: 3, takes place with an amino acid having an equivalent functionality as regards its hydrophobic, charge or spacing properties. The choice is made, for example, from the group of the hydrophobic amino acids, between alanine, isoleucine, leucine, methionine, phenylalanine, proline, tryptophan and valine; from the group of uncharged polar amino acids, asparagine, cysteine, glutamine, glycine, serine, threonine and tyrosine; from positively charged amino acids, arginine, histidine and lysine; from negatively charged amino acids, aspartic acid and glutamic acid; and from the group of amino acids with equivalent spacing, alanine, glycine and serine.

A post-translational modification such as disulfide bridge formation between the cysteines of the peptide stabilizes the folded conformation of the xenoxins, thereby enabling their pharmacological activities to be exercised.

The different sulfide bridges do not form in random fashion. When the amino acid sequence is allowed to coil, the disulfide groups which link up are the ones from two neighboring cysteines in the folded peptide. For this reason, the conformation of the peptide skeleton may be described by the arrangement of the disulfide bridges. To this end, the links which have formed between the cysteines in the folded peptide are described, and an indication is given of the number of amino acids between the different successive cysteines in the primary sequence of the peptides.

Hence there exists a twofold structural similarity between the peptides of the same family, in particular in respect of the peptide skeleton and in respect of the identity of amino acids. Thus, when two peptides of the same family are compared, they may be found to possess amino acid sequences with a significant disparity, to see [sic] even an identity of amino acids as low as 40%. In contrast, the similarity of the arrangement of the cysteines involved in the formation of the disulfide bridges will be striking.

The xenoxins according to the invention, in complete form or in fragment form, may also be introduced into more complex chemical or physicochemical structures intended to facilitate their activity or to endow them with advantageous therapeutical properties, such as, for example, the retard or protected form.

The invention also relates to unmodified, for example unglycosylated, xenoxins. However, the scope of protection also includes modified xenoxins, for example glycosolyated or deglycosolyted products or products modified with polyethylene glycol.

The xenoxins according to the present invention may be isolated according to the following method:

a. the matter secreted by frog's skin is divided into fractions by precipitation using ammonium sulfate or an equivalent precipitating agent, b. the precipitates which form at between 30% and 70% saturation with ammonium sulfate, and preferably between 30% and 60%, or under equivalent conditions, are subjected to gel permeation chromatography, and c. the peptide fraction which elutes late is harvested.

If so desired, the mixture of xenoxins thereby obtained may then be purified, in particular by cation exchange HPLC followed by reversed-phase HPLC.

According to a preferred aspect of the present invention, the matter secreted by frog's skin originates from *Xenopus laevis.*

In the method according to the invention, the peptide fraction is advantageously precipitated using ammonium sulfate. However, other precipitating agents may be used, such as polyethylene glycol, ethanol or sodium sulfate. It is for a person skilled in the art to choose the range of saturation precipitating agent needed to obtain the precipitates free, on the one hand from proteins, and on the other hand from peptides with molecular weights below 10 kDa, and preferably 8 kDa.

Normally, gel permeation chromatography enables molecules to be separated in accordance with their molecular size. In the method according to the invention, this chromatography enables all molecules of large molecular size to be eliminated from the peptides in question, harvesting only the fraction which elutes late from the column.

As a result, every type of permeation gel having a fractionation range above 10 kDa may be used. On the market, this type of gel is available under the name, for example, of Sephacryl S200 (Pharmacia), Sephadex (Pharmacia), Fractogel (Merck) or Toyopearl (Toso Haas).

It is also possible to synthesize the peptides according to the invention chemically by synthesis methods known to a person skilled in the art. By way of reference, E. Bayer, Angew. Chem. Int. Ed. Engl. 30, (1991), P 113 will be mentioned.

The present invention also relates to the expression of xenoxins in the cell systems other than the natural cell system from which they originate.

To this end, the invention also relates to the isolated DNA sequences coding for said xenoxins, as well as to cassettes for the expression of said sequences providing for their expression in the desired cell.

Isolated DNA fragment is understood to mean a DNA fragment which is no longer associated with the set of natural regions which control its expression in the organism from which it originates, that is to say, in the case of the example mentioned below, from *Xenopus laevis.*

Among isolated DNA sequences which comprise a sequence coding for a peptide according to the invention, special mention should be made of the DNA which is recorded in the sequence identification listing under the number SEQ ID NO: 1, and more especially the portion of SEQ ID NO: 1 from position 39 to 290 and the portion of SEQ ID NO: 1 from position 93 to 290.

The invention relates to cassettes for the expression of said DNA sequences coding for peptide according to the invention.

Such an expression cassette comprises, in particular, an isolated DNA fragment which is placed under the control of elements permitting its transcription and translation in the host cell in question.

These control elements are essentially a suitable transcription promoter together with translation initiation and termination codons. In some cases, it is also advantageous to add a transcription terminator and a signal peptide, or pre sequence, optionally followed by a pro sequence. Preference will be given most especially to the pro sequence of *Phormia terranovae* defensin A (Dimarcq et al., EMBO J. 9 (1990) p. 2507), which is functional in eukaryotic cells and in particular yeasts such as *Saccharomyces cerevisiae.*

The invention also relates to a cell which is transformed with an expression cassette which comprises a DNA fragment according to the invention. The expression cassette may be either integrated in the genome of the cell or carried by a suitable expression vector such as, for example, a plasmid or a viral vector.

The present invention also relates to the use of expression vectors capable of being administered in order to produce xenoxins in situ in humans or animals, in particular when the vector is a viral or synthetic vector (for example mixtures of lipids, such as liposomes).

Lastly, the present invention relates to a method for preparing a peptide according to the invention, which consists in culturing a transformed cell according to the invention and in harvesting said peptide from the culture.

The technologies permitting the cloning of a foreign gene into prokaryotic or eukaryotic host cells and its expression therein are known to a person skilled in the art. They will be illustrated in the examples below, on the understanding that other vectors and other host cells may be used. A person skilled in the art is quite clearly capable of choosing the appropriate transcription promoter in accordance with the host in which it is desired to express the DNA fragment, and in accordance with the vector into which the expression cassette has to be inserted.

According to a preferred method for preparing a peptide according to the invention, the isolated DNA fragment is expressed in host cells which permit secretion of the peptides synthesized into the culture medium and enable the formation of the disulfide bridges to be effected. As an example, the host cells of prokaryotes such as *E. coli,* of lower eukaryotes such as *Saccharomyces cerevisiae* or of higher eukaryotes such as humans or animals or plants may be mentioned.

To direct a peptide according to the invention into the secretion system of the host cells, provision is made in the expression cassette for a sequence coding for a precurser of the peptide. Said precursor essentially comprises a peptide according to the invention in mature form and a signal peptide bound through a peptide bond to its $NH_2$-terminal end. A signal peptide generally contains an amino acid sequence which is mainly hydrophobic and has the function of promoting secretion. During the process of translocation, this signal peptide will be cleaved by an enzyme, the signal peptidase. The molecule secreted into the culture medium or into the host's periplasm is thus a mature peptide.

The signal peptide preferably used originates from genes that are known to code for a product which is secreted effectively. As an example, the signal peptides of SUC2 periplasmic invertase (R. A. Smith et al., Science 229, (1985), p 1219; C. N. Chang et al., Mol. Cell. Biol. 6, (1986), p 1812), as well as the "killer" toxin signal peptides of *Kluyveromyces lactis* (C. Baldazi et al., EMBO J. 6, (1987), p 229) or of *Saccharomyces cerevisiae* (M. Tokunaga et al., Nucleic Acids Res. 16, (1988), p 7499), may be mentioned. As a guide, it may be pointed out, however, that the signal peptide of the BGL2 gene originating from *S. cerevisiae* (T. Achstetter et al., Gene 110, (1992) p 25), and used in the examples below, enables very good results to be obtained. Moreover, the natural signal peptide of the xenoxins may also be employed.

In some cases, the peptide obtained may not display the correct conformation; it may then be necessary to carry out its rearrangement by chemical methods entailing, for example, dissolution and refolding using pH conditions and urea, for example.

The present invention also relates to the anti-xenoxin monoclonal or polyclonal antibodies which may be obtained by known methods, as well as to their application both in therapy and in the diagnostic field to identify or quantify xenoxins in humans or in animals. The choice of the technique to be employed is wide and within the capacity of a person skilled in the art. ELISA, labeling or alternatively fluorescent techniques may be mentioned in particular.

Hence the present invention also relates to diagnostic kits using xenoxins or the corresponding antibodies.

The peptides according to the invention have therapeutic applications in mammals, and in particular in humans, in view of their properties of being able to influence the functioning of transmembrane ion channels, and of activin, without having neurotoxic acitivity.

Consequently the invention also relates to:

a pharmaceutical composition which comprises as active agent at least one peptide according to the invention;

the therapeutic use of a peptide according to the invention;

The pharmaceutical composition according to the invention is intended especially for the preventive or curative treatment of disorders such as, for example, cardiac arrhythmias due to hyper- or hypotension; fibrocystic diseases of genetic origin such as mucoviscidosis of the pancreas, better known by the name cystic fibrosis; disturbances associated with an imbalance of human chorionic gonadotrophin during pregnancy; disorders due to an imbalance in the secretion of the hormones FSH, STH and ACTH (for follicle stimulating hormone, somatotropic hormone and adrenocorticotropic hormone, respectively, in English); the pharmaceutical compositions according to the invention also enable erythropoiesis to be regulated.

The pharmaceutical compositions containing the peptides according to the invention may be administered via the route best suited to its [sic] final destination, in particular via the oral, parenteral or rectal route.

The pharmaceutical compositions which can be used for oral administration can be solid or liquid, for example in the form of tablets (coated or otherwise), pills, dragees, gelatin capsules, solutions, syrups, and the like.

Similarly, the compositions which can be used for parenteral administration are the pharmaceutical dosage forms known for this type of administration, for example aqueous or oily solutions, suspensions or emulsions, which are suitable, inter alia, for intramuscular, intravenous, intraperitoneal or subcutaneous injection or cutaneous or transmucosal applications, for example by spray, ointments, and the like.

For rectal administration, the compositions containing the compounds of the invention generally take the form of suppositories.

The compounds according to the invention may also be prepared in a controlled-release form and, in accordance with the administration route adopted, in a suitable protected form so as to avoid an excessively rapid degradation of the peptide.

The pharmaceutical dosage forms such as injectable solutions, injectable suspensions, tablets, drops, suppositories, and the like, are prepared according to the methods commonly used by pharmacists. The pharmaceutical dosage forms also comprise compositions which enable the active peptide to be delivered gradually. The compounds of the invention are mixed with a pharmaceutically acceptable, nontoxic solid or liquid vehicle and, where appropriate, with a dispersing agent, a disintegrating agent, a stabilizing agent, and the like. Sweetening agents, coloring agents, and the like, may, for example, be added thereto. The percentage of active product in the pharmaceutical compositions can vary within very wide limits, depending on the patient and the mode of administration, especially according to the frequency of administration.

The examples which follow illustrate the present invention without limiting it; reference is made therein to FIGS. 1 to 4.

FIG. 1 shows a Coomassie blue-stained SDS-PAGE of two different stages of purification. (1) peptide fraction harvested after Sephacryl S-300 gel permeation chromatography; (2) Molecular weight markers from bottom to top: lysozyme (14300), trypsin inhibitor (21500), carbonic anhydrase (30000), ovalbumin (46000), bovine serum albumin (69000), phosphorylase b (92500) and myosin (200000); (3) xenoxin-1 purified by cation exchange and reversed-phased HPLC according to Example 1 below.

FIG. 2 shows an elution profile obtained after cation exchange HPLC of the peptide fraction originating from *Xenopus laevis* skin secretion, obtained by ammonium sulfate precipitation followed by gel permeation chromatography under the condition of the Example 1 which is recorded below. The fractions which contain xenoxin-1, xenoxin-3 and xenoxin-2, respectively, are indicated by successive arrows.

FIG. 3A shows the alignment of (a) xenoxin-1 with (b) the cytotoxin originating from *Naja naja kaouthia, Naja naja siamensis,* a one-eyed cobra (S. Inoue et al., FEBS Lett. 218, (1987), p 17) and (c) the short neurotoxin d of *Laticauda colubrina,* a yellow-lipped sea krait (N. Tamiya et al., Toxicon (Suppl. 3), (1983), p 445). Gaps (–) are introduced and the disulfide bridges indicated.

FIG. 3B shows the number of amino acids between the successive cysteines in the primary sequences for the three families of peptides, xenoxins, cytotoxins and short neurotoxins, respectively.

FIG. 4 shows the alignment of xenoxin-1 with 27 amino acids of the N-terminal binding site of 116 residues of the human activin receptor.

EXAMPLE 1

Purification and Characterization of Xenoxins

1.1 Isolation and Purification of Xenoxins

*Xenopus laevis* (Herpetologic Institute, DeRover, Netherlands) is maintained in aerated troughs fed with ground pig's liver. Every three weeks, the animals are subjected to a mild electric shock (15 V) and their skin secretions are harvested in 0.9% NaCl solution according to the method described by C. Mollay et al., Eur. J. Biochem, 160, (1986), p 31. The mucous thus extracted is subjected to two successive extractions with an equal volume of n-butanol. The insoluble fraction is removed by centrifugation for 15 minutes at 15,000 rpm (Sorvall RC-5B, SS34 rotor) . Ammonium sulfate is then added to the supernatant, and the material precipitating at between 30 and 60% saturation is recovered. This precipitate is dissolved and dialyzed in 50 mM ammonium acetate, pH 5.0 and subjected to gel permeation chromatography using a Sephacryl S-300 column (2.7 cm×120 cm; Pharmacia) equilibrated with the same buffer. The peptide fraction is detected at 280 nm and elutes late in the form of a broad peak. Only this late fraction is collected and lyophilized.

Figure 1:
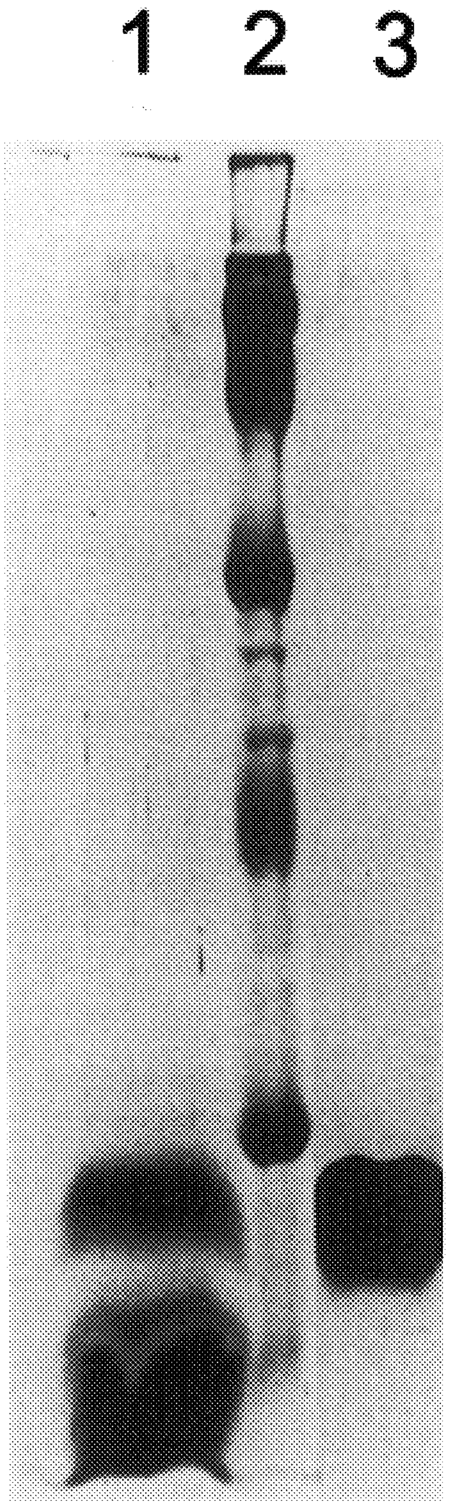

A Coomassie blue-stained SDS-PAGE is set up in order to verify that molecules of molecular weight above 10 kDa are eliminated (see FIG. 1).

The lyophilized peptide fraction is taken up in 50 ml of 5% acetonitrile in 20 mM ammonium acetate at pH 4.6, and then centrifuged for 15 minutes at 15,000 rpm (Sorvall RC-5B, SS34 rotor). The supernatant is filtered through a 0.22 μm Millex GV filter (Millipore), and 5-ml aliquots are frozen at −80° C.

A 5-ml aliquot of the solution is diluted in 90 ml of CEI buffer (25% acetonitrile in 5 mM monobasic potassium phosphate adjusted to pH 3.0 using phosphoric acid). The conductivity of the solution is adjusted to 8 mS using CE1 buffer and, if necessary, the pH is adjusted to 3.0 using phosphoric acid. The solution thereby obtained is then separated into three aliquots, which are subjected successively to separation by cation exchange HPLC (high performance liquid chromatography) with UW detection at 215 nm, in the following manner:

the aliquot is loaded onto an HPLC column (polysulfoethyl aspartamide SCX; 9.4 mm×200 mm; The Nest Group) at a flow rate of 1.6 ml/minute;

the column is washed with CE1 buffer until the base line at 215 nm has stabilized;

a 0 to 100% gradient of CE2 buffer (600 mM potassium chloride in CEI buffer) is applied over 40 minutes in order to elute the adsorbed material, which is collected manually in 1.6-ml fractions;

the column is washed with CE2 buffer for 10 minutes;

a 100% CE2 buffer to 100% CE1 buffer gradient is applied over 5 minutes; and the column is washed with CE1 buffer for 15 minutes.

Figure 2:
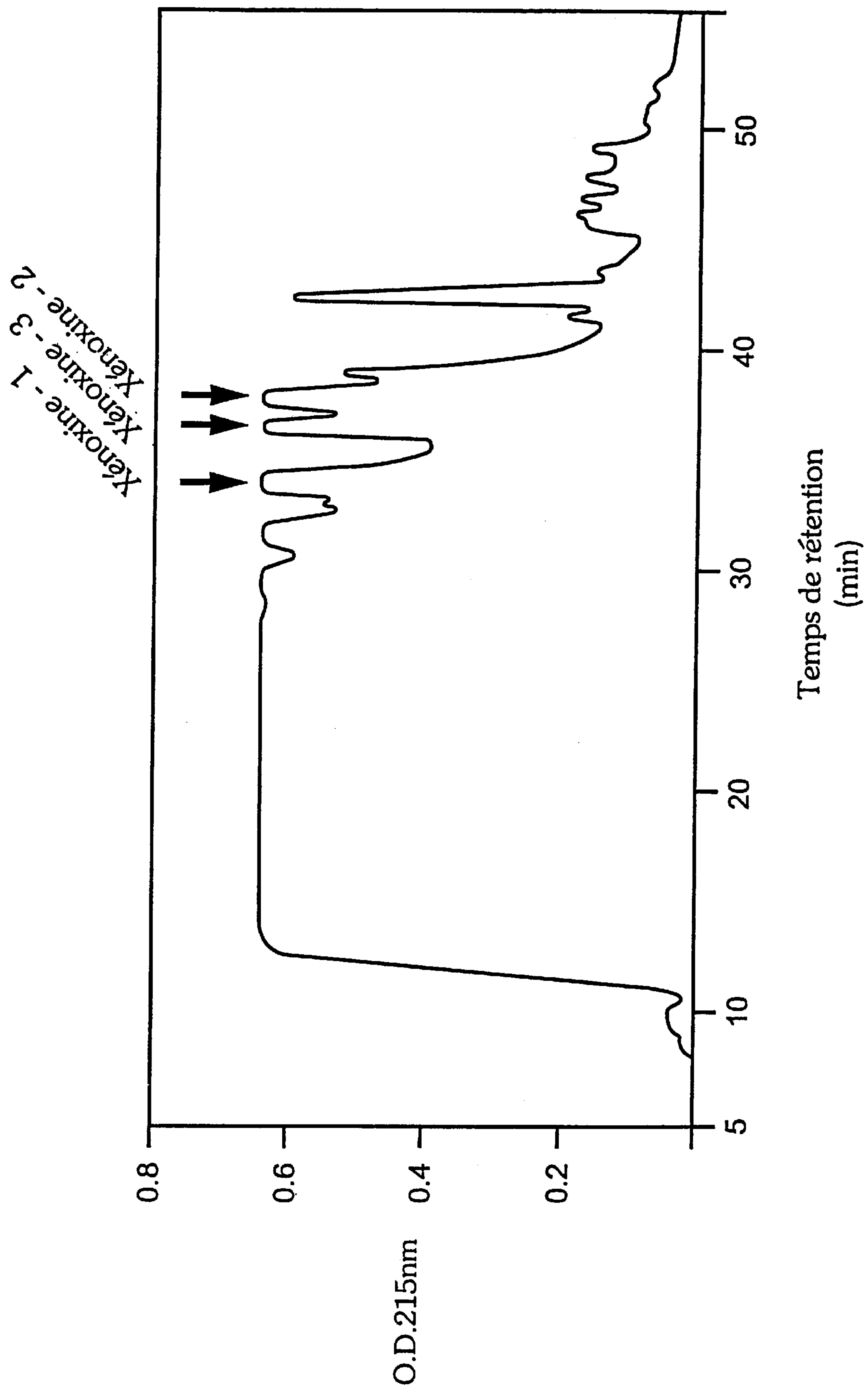

There are obtained, respectively, xenoxin-1 which elutes at between 362 and 392 nM potassium chloride after 33.3 to 35.5 minutes, xenoxin-3 (398–415 mM; 35.9–371 minutes) and xenoxin-2 (415–435 mM; 37.1–38.6 minutes), which are indicated by the successive arrows on the diagram in FIG. 2.

A step of separation in reversed-phase HPLC (Hewlett Packard 1090A) with UW detection at 205 nm is then carried out. To this end, the individual fractions emerging from the cation exchange HPLC chromatography are loaded directly onto a Vydac $C_{18}$ HPLC column (10 mm×250 mm; Vydac Separation Group) equilibrated with RP1 buffer (0.10% (v/v) trifluoroacetic acid (TFA) in water deionized by the Millipore reactive water preparation system (Milli Q water)) at a flow rate of 1.5 ml/minute.

For each fraction loaded, the xenoxins are eluted from the column according to the following procedure:

100% RP1 buffer for 5 minutes in order to restabilize the column;

a 100% RP1 buffer to 71.4% RP2 buffer (30:70:0.10 (v/v/v) of Milli Q water/acetonitrile/TFA) gradient is applied over 100 minutes;

the column is washed with 71.4% RP2 buffer for 10 minutes;

a 71.4% RP2 buffer to 100% RP1 buffer gradient is applied over 5 minutes; and the column is washed with 100% RP1 buffer for 15 minutes.

The fractions are collected manually, and the desalted and purified xenoxins are concentrated using a Speed Vac Concentrator (Savant) and stored at −20° C.

From one equivalent of skin secretions from 150 *Xenopi laevis,* 800 μg of xenoxin-1, 650 μg of xenoxin-2 and 200 μg of xenoxin-3 are thereby obtained.

1.2 Characterization of the Xenoxins

1.2.1 Reduction and Alkylation

50 μg of xenoxins purified and concentrated according to Example 1.1 are taken up in an alkylation buffer (250 mM Tris-HC1, pH 8.5; 6M guanidinium chloride; 1 mM EDTA) at a concentration of 250 μg/ml, then homogenized in a vortex mixer and sonicated for 5 minutes. Thereafter 5 μl of 20:80 (v/v) β-mercaptoethanol in Milli Q water are added, and the mixture is placed under argon and left at 37° C. After 2 hours, 10 μl of 4-vinylpyridine (4VP; Janssen) are added, and the mixture is again placed under argon and left at room temperature. After 2 hours, the reaction mixture is frozen and kept at −20° C. until it is used for digestion or desalting.

1.2.2 Clostripain (CL), Trypsin (T) or Cyanogen Bromide (CNBr) Digestion.

Clostripain (Sigma) is activated at a concentration of 1 mg/ml in CL buffer (100 mM Tris-HC1, pH 7.5; 1 mM calcium dichloride, 2.5 mM DTT) at 37° C. for 2 hours. 12 μg of xenoxin prepared according to Example 1.1. (alkylated with 4 VP according to Example 1.2.1, or unalkylated) are incubated in CL buffer for 16 hours at 37° C. at a concentration of 150 μg/ml and a protease/substrate weight ratio of 1:10. 8 μl of glacial acetic acid and 70 μl of RP1 buffer (see above) are then added. The solution thereby obtained is then used to determine the peptide map by reversed-phase HPLC chromatography as described in Example 1.2.3 below.

Trypsin (1 mg/ml in 1 mM HCl) (Boehringer) is diluted 10-fold in TR buffer (100 mM N-ethylmorpholine-HCl, pH 8.3; 0.1 mM calcium dichloride). 25 μg of xenoxin prepared according to Example 1.1. (alkylated with 4 VP or unalkylated) are incubated in TR buffer for 16 hours at 37° C. at a concentration of 240 μg/ml and a protease/substrate weight ratio of between 1:5 and 1:100. 2 μl of pure TFA buffer and 100 μl of RP1 buffer are then added, and the solution thereby obtained is used to determine the peptide map by reversed-phase HPLC chromatography as described in Example 1.2.3.

40 μl of a 1% solution (weight/volume) of CNBr (Pierce) in 70% formic acid are added to 25 μg of xenoxin prepared according to Example 1.1. (alkylated with 4 VP or unalkylated). Reaction is continued for 16 hours after adding 300 μl of Milli Q water. The reaction mixture is dried using a Speed Vac Concentrator. 250 μl of RP1 buffer are added. The solution thereby obtained is used to determine the peptide map by reversed-phase HPLC chromatography as described in Example 1.2.3.

1.2.3. Determination of the Peptide Map by Reversed-phase HPLC Chromatography.

Peptide mapping is carried out by reversed-phase HPLC chromatography using an HPLC 1090A unit (Hewlett-Packard) with UV detection at 205 nm.

The intact xenoxin molecules, their proteolytic fragments and also their equivalents alkylated with 4 VP are loaded onto a Superspher 100$C_{18}$ HPLC column (4 mm×125 mm; Merck) equilibrated with 10 mM TFA in 10:90 (v/v) acetonitrile/Milli Q water at a flow rate of 1 ml/minute. The peptides are then eluted according to the following protocol:

the column is washed with 10 mM TFA in 10:90 (v/v) acetonitrile/Milli Q water for 15 minutes; and a linear gradient up to 10 mM TFA in 50:50 (v/v) acetonitrile/Milli Q water is applied over 40 minutes.

The eluted fractions are collected manually and concentrated using a Speed Vac Concentrator.

The observed retention times are recorded in Tables I, II and III below.

1.2.4. Determination of the Amino Acid Sequence

The peptides obtained according to Example 1.2.3 are solubilized in 80% formic acid solution, and determination of the N-termination sequence is carried out using a type 477A protein sequencer coupled to an HPLC phenylthiocarbamic amino acid analyser (Applied Biosystems Inc.) according to standard procedures. The results of the sequencing are presented in Tables I, II and III below.

TABLE I

| Peptide [1] | retention time (minutes) | AMINO ACID SEQUENCE (10 20 30 40 50 60) |
| --- | --- | --- |
| xenoxin-1, alkylated[a] | 37.5 | LKCVNLQANGIKMTQECAKEDTKCLTLRSLKKTLKFC |
| xenoxin-1, alkylated fragment CNBR1[b,c,d] | 34.0 | LKCVNLQANGIKXXQECAKEDTKCLTLRSLKKTLKFCAXXXTC<br>TQECAKEDTKCLTXRSLKKTLKFCAXGRTCT<br>LKCVNLQA |
| xenoxin-1, alkylated fragment CL1[b] | 27.7 | SLKKTLKFCASG<br>TXTTMK<br>IMSLPGEQITXXEGNMXNA |
| xenoxin-1 fragment T1[b,d] | 33.4 | SLPGEQITCCEGN<br>IMSLPGEQITXXEGNMXNA<br>KIMSLPGEQITCCEGN |
| xenoxin-1, alkylated fragment CNBR2[b,c] | 28.2 | IMSLPGEQITCCEGNMCN |
| xenoxin-1, alkylated fragment CL2 | 32.9 | |
| xenoxin-1 | 40.0 | LKCVNLQANGIKMTQECAKEDTKCLTLRSLKKTLKFCASGRTCTTMKIMSLPGEQITCCEGNMCNA |

[1] CNBR, CL or T specify the proteolytic method used
[a]Complete molecule, only the analysed portion is presented
[b]Two peptide sequences are read in parallel
[c]A peptide derived from an incomplete cleavage
[d]The residues marked X are not identifiable

TABLE II

| Peptide [1] | retention time (minutes) | AMINO ACID SEQUENCE (10 20 30 40 50 60) |
| --- | --- | --- |
| xenoxin-2, alkylated[a] | 37.5 | LKCVNLQANGIKMTQECAKEDNKCLTLRSLKKTLKFCAXDRICKTMKIMSLPGEXI |
| xenoxin-2[a,b] | 40.0 | LKXVNLQANGIKMTQEXAKEDNKXLTLRSLKKTLKFCASDXIXKTMK<br>ITCCEGNMCNA |
| xenoxin-2, alkylated fragment CL3 | 23.0 | IMSLPGEK |
| xenoxin-2 fragment T3 | 28.0 | |
| xenoxin-2 | 40.0 | LKCVNLQANGIKMTQECAKEDNKCLTLRSLKKTLKFCASDRICKTMKIMSLPGEKITCCEGNMCNA |

[1] CL or T specify the proteolytic method used
[a]Complete molecule, only the analysed portion is presented
[b]The residues marked X are not identifiable

TABLE III

| Peptide [(1)] | retention time (minutes) | AMINO ACID SEQUENCE 10 20 30 40 50 60 |
|---|---|---|
| xenoxin-3, alkylated[a,b,c] | 35.5 | LXCVNLQANGXKMXQECXKE<br>KCVNLQANGVKMTQECAKED<br>CVNLQANGVKMTQECAKEDT |
| | | FCASDR |
| xenoxin-3, alkylated fragment T4 | 7.0 | |
| | | IASLPGEQITCCEGNMCNA |
| xenoxin-3, alkylated fragment T5 | ? | IASLPGEQITXXEGNMXNA |
| xenoxin-3, alkylated fragment T6[b] | ? | |
| xenoxin-3[d] | 40.0 | LKCVNLQANGVKMTQECAKEDTKCLTLRSLKKTLKFCASDRICKTMKIASLPGEQITCCEGNMCNA |

[(1)] T specifies the proteolytic method used
[a]Complete molecule, only the analysed portion is presented
[b]The residues marked X are not identifiable
[c]Three peptide sequences are read in parallel
[d]The amino acids in italics are deduced from the sequences of xenoxin-1 and xenoxin-2

1.2.5 Mass Spectrometry

Mass spectrometry measurements are performed by ESMS (electrospray mass spectrometry) on a VC Bio Tech BioQ type mass spectrometer (VC Biotech Ltd.). The protocols used are known to a person skilled in the art and are recorded, for example, in A. Van Dorsselaer et al., Biomed. Environ, Mass Spectrom, 19, (1990), p 692. The calculated molecular masses are given as mean values based on the following values for the atomic mass of the elements C, H, N, O and S: C=12.011, H=1.0079, N=14.0067, 0=15.9994 and S=32.06.

The results are presented in Table IV below.

TABLE IV

MASS SPECTROMETRY

| Peptide | Experimental molecular mass | Calculated molecular mass |
|---|---|---|
| xenoxin-1 | 7228.3 ± 0.1 Da[a] | 7227.6 Da[b] |
| xenoxin-1, alkylated | 8077.7 ± 0.4 Da[c] | 8076.7 Da[d] |
| xenoxin-1, T1 | 2693.5 ± 0.2 Da | 2694.6 Da[e] |
| xenoxin-1, T2 | 1662.0 ± 0.2 Da | 1662.0 Da[f] |
| mixture of tryptic | 2329.2 ± 0.6 Da | 2329.7 Da[g] |
| fragments | 1164.5 ± 0.4 Da | 1164.3 Da[h] |
| xenoxin-1, alkylated | 744.4 Da | 744.8 Da[i] |
| | 709.4 Da | 709.5 Da[j] |
| xenoxin-2 | 7337.5 ± 0.5 Da | 7337.8 Da[b] |
| xenoxin-2, alkylated | 8188.7 ± 0.5 Da[c] | 8186.9 Da[d] |
| xenoxin-2, fragment T2' | 1661.9 ± 0.6 Da | 1662.0 Da[f] |
| mixture of tryptic | 1473.0 ± 0.2 Da | 1473.7 Da[k] |
| fragments | 1164.7 ± 0.2 Da | 1164.3 Da[h] |
| xenoxins-2[sic], | 873.5 Da | 874.1 Da[i] |
| alkylated | 709.5 Da | 709.5 Da[j] |
| xenoxin-3 | 7251.2 ± 0.4 Da | 7250.6 Da[b] |
| xenoxin-3, alkylated | 8100.6 ± 0.8 Da[c] | 899.8 Da[d] |

[a]Mass corresponding to the predominant signal; a less intense signal gives a mass of 7243.8 ± 0.4 Da, probably due to the addition of an oxygen atom to the first methionine.
[b]Assuming that the 4 disulfide bridges are intact.
[c]Indicating 8 4VP compounds per protein; for xenoxin-1, a less intense signal gives a mass of 8091.8 ± 0.9 Da, probably due to the addition of an oxygen atom.
[d]Reduced xenoxin, alkylated with 8 4VP components.

TABLE IV-continued

MASS SPECTROMETRY

| Peptide | Experimental molecular mass | Calculated molecular mass |
|---|---|---|

[e]TCTTMK, cysteine linked to IMSLPGEQITCCEGNMCNA; assuming that the 2 disulfide bridges are intact.
[f]CVNLQANGIK, cysteine linked to CLTLR, assuming that the disulfide bridge is intact.
[g]IMSLPGEQITCCEGNMCNA, alkylated with 3 4VP compounds.
[h]CVNLQANGIK, alkylated with one 4VP compound.
[i]FCASGR, alkylated with one 4VP compound.
[j]CLTLR, alkylated with one 4VP compound.
[k]ITC.CEGNMCNA, alkylated with 3 4VP compounds.
[l]IMSLPGEK.

EXAMPLE 2

Cloning of Complementary DNA Coding for Xenoxins

For further details regarding the general techniques of nucleic acid manipulation and molecular cloning which are not detailed in the example which follows, reference may be made to the work by Maniatis et al., (Laboratory Manual, Cold Spring Harbor Laboratory Press, Cold Spring Harbor, N.Y. (1989)).

2.1. Synthesis of Oligonucleotide Primers

Using an ABI 380B oligonucleotide synthesizer (Applied Biosystems Inc.) according to the standard procedures recommended by the manufacturer, 0.2 μmol of the following oligonucleotides are synthesized. Degenerate bases are expressed according to their one-letter code of the International Union of Biochemistry (IUB); I corresponds to inosine.

OTG3278 (5'-ATGTCGACCARGARTGYGCIAARGARGA-3'), i.e. Q-E-C-A-K-E-D sense strand with the addition of a SalI restriction site at the 5' end so as to facilitate subsequent subcloning (SEQ ID NO:26); and OTG3279 (5'-ATAAGCTTCACATRTTICCYTCRCARCA-3'), i.e. C-C-

E-G-N-M-C antisense strand with the addition of a HindIII site at the 5' end so as to facilitate subsequent subcloning (SEQ ID NO: 27).

After deprotection, the oligonucleotides are purified on $\mu$-Bondapak $C_{18}$ (3.5 mm×300 mm; Waters) using a 20%–30% acetonitrile gradient in the presence of 100 mM acetic acid/triethylamine, pH 6.9. The oligonucleotides are detritylated according to standard conditions well known to a person skilled in the art, and quantified by means of their Uv spectrum between 230 and 340 nm.

2.2. Gene Amplification

*Xenopus laevis* messenger RNA is obtained according to the method described in K. Richter, et al., J. Biol. Chem. 261, (1986), p 3676, and is then subjected to reverse transcription initiated by degenerate primers. The cDNA which will serve as template for the amplification is thereby obtained. A step of gene amplification by PCR (polymerase chain reaction) is then carried out on 0.5 $\mu$g of cDNA in 50 $\mu$l containing 250 ng of the oligonucleotides OTG3278 (sense strand) and OTG3279 (antisense strand) synthesized according to Example 2.1, as well as 10 mM Tris-HCl, pH 8.3, 10 mM potassium chloride, 1.6 mM magnesium dichloride, 1 mM DTT, 200 $\mu$M each of the deoxyribonucleoside triphosphates (clATP, dCTP, dGTP and dTTP) (Pharmacia) and 2.5 units of AmpliTaq DNA polymerase (Perkin Elmer Cetus). One unit being [sic] the amount of enzyme which permits the synthesis of 10 nmol of DNA during 30 minutes of incubation, 30 amplification cycles are carried out according to the following protocol:

In the first 5 cycles:

denaturation at 93° C. for 1 minute (3 minutes in the first cycle);

hybridization of the primers at 50° C. for 2 minutes;

polymerization performed at 72° C. for 30 seconds, with a temperature rise of 1° C. per 20 seconds;

In the remaining 25 cycles:

denaturation at 93° C. for 1 minute;

hybridization at 60° C. for 1 minute; and polymerization at 72° C. for 45 seconds.

2.3. Analysis

In electrophoresis on agarose gel (1%), a 5 $\mu$l aliquot of the PCR product displays a broad band of approximately 120 base pairs.

2.4. Cloning of the PCR cDNA

The remaining DNA is subjected to digestion using the restriction enzymes HindIII and SalI (Gibco-BRL), and the DNA fragments are then separated according to their size using low-melting-temperature agarose (Sigma agarose type II). The DNAs thus separated are purified and cloned into an M13 bacteriophage according to standard procedures. The PCR cDNA fragments thus cloned are used as probe for screening of the *Xenopus laevis* skin cDNA library.

2.5. Screening of the *Xenopus laevis* Skin cDNA Library.

A $^{32}$p-labeled probe is prepared using the PCR cDNA fragment PCR1, from a clone prepared according to Example 2.4. The sequence of the PCR1 insert is shown in the sequence listing under the number SEQ ID NO: 28. PCR1 is labeled with $\alpha[^{32}P]$ dATP [sic] (Amersham) according to the random primer method (Boehringer Mannheim).

For screening, the *Xenopus laevis* skin cDNA library constructed in the expression vector λgt11, according to Kuchler et al., J. Biol. Chem. 265, (1990), p 11731, is used. Dishes containing approximately $2\times10^4$ plaques of phage are prepared, and a blot is made on a BA85 nitrocellulose filter (Schleicher & Schüll).

The blotted filters are then hybridized with the $^{32}$P-labeled PCR1 probe in 2×SET (sodium chloride-EDTA-Tris-HCl), 10×Denhardt's solution and 0.1% SDS at 55° C.

Positive clones are used in two consecutive screenings.

2.6. Sequencing of the CDNA Clones

The DNA of positive phages is isolated, and the CDNA inserts are subcloned into M13TG130 vectors (Kieny et al., Gene 26, (1983), p 91) according to standard methods.

The sequencing of these CDNA inserts is carried out according to the enzymatic methods of Sanger et al., Proc. Natl. Acad. Sci. USA, 74, (1977), p 5463, using the Sequenase Kit (US Biochemical Corp.).

The nucleotide sequence of one clone with a cDnA insert consisting of 462 base pairs was established. This sequence is shown in the sequence listing under the number SEQ ID NO: 1, and contains an open reading frame coding for pre-xenoxin-1 which contains 84 amino acids. The pre-xenoxin-1 peptide as deduced from the cDNA sequence begins with an initiation methionine encoded by the ATG codon (p 39 to 41), followed by a signal peptide of 18 amino acids which precedes the mature xenoxin-1 sequence. The amino acid sequence of mature xenoxin-1 which is deduced corresponds exactly to the complete amino acid sequence determined by Edman degradation of xenoxin-1 purified according to Example 1.1, and shown in the sequence listing under the number SEQ ID NO: 3.

The polyadenylation signal AATAAA occurs 12 base pairs upstream of the 3' end.

2.7. Analysis of the Peptide Sequences

The sequences of the xenoxines were compared with the SWISS-PROT/PIR/GBTRAN release 24 data bank using PROSCAN, Ver.6.0. of the DNA STAR software (DNA STAR Inc).

This research only made it possible to identify families of peptides which have a structural similarity in respect of the peptide skeleton, but not in respect of the identity of amino acids. As illustrated in FIG. 3A, the identity is only 25.9% with a representative member of the cytotoxin family, and only 21.3% with a short neurotoxin although the arrangement of the disulfide bridges is the same. Apart from the cysteines, only $Asn^5$, $Thr^{14}$ and $Asn^{71}$ are conserved in the three families of peptides. The $Gly^{20}$, $Pro^{50}$ and $Lys^{51}$ which are common to the cytotoxins and to the short neurotoxins are nonconservative substitutions compared with the xenoxins. $Arg^{41}$ and $Gly^{42}$ are deleted in the xenoxins.

As regards the number of amino acids between the cysteines, reference may be made to FIG. 3B. For the three families, the number is comparable on the N-terminal side up to $Cys^3$ and from $Cys^6$ up to the C-terminal side. In contrast, in the xenoxins, the number of residues between $Cys^3$ and $Cys^4$ is smaller, and between $Cys^4$ and $Cys^5$ and between $Cys^5$ and $Cys^6$ it is larger.

As illustrated in FIG. 4, the C-terminal portion of the xenoxins ($Cys^{37}$ to $Asn^{65}$, 29 residues) comprising $Cys^4$ to $Cys^8$ share a 50% identity of amino acids with 27 amino acids ($Cys^{85}$ to $Asn^{111}$) of the human activin receptor. On the N-terminal side of the xenoxins, no sequence identity is to be found, even in respect of the cysteines.

EXAMPLE 3

Preparation of Recombinant Xenoxins 3.1. Construction of a Vector for the Expression of Xenoxin The xenoxins according to the invention may be obtained by genetic engineering techniques, in particular using *Saccharomyces cerevisiae* yeasts as host cell.

To this end, a DNA fragment coding for mature xenoxin-1 as identified under the number SEQ ID NO: 1, extending from the base at position 93 to the base at position 290, and cloned into the bacteriophage M13TG131 (M. P. Kieny et al., Gene 26, (1983), p 91), is synthesized.

A plasmid for the expression of xenoxin-1 which permits synthesis and secretion by *S. cerevisiae* is constructed according to International Patent Application PCT/FR90/00306, which describes signal peptides which are useful for the secretion of a heterologous protein by yeast.

The 1045-base pair SphI-SmaI fragment of the bacteriophage M13TG3846 described in Example 1.E. of said international patent application is transferred to the vector M13TG3869 (described in Example 1.D. of the same application) previously digested with SphI and SmaI. The vector M13TG4803 is thereby obtained, which carries:

the MFα1 gene promoter followed by an ATG codon, the sequence XII (see PCT/FR/90/00306), the mutated "pro" sequence of the MFα1 gene followed by the codons coding for Lys-Arg, the sequence coding for rHV2Lys47.

In order to replace the sequence coding for rHV2Lys47 by the one coding for xenoxin-1, a HindIII site is introduced into the sequence coding for mutated "pro" of MFα1 according to Example 3.B. of the international application.

A HindIII-BamHI fragment which carries the sequence coding for xenoxin-1 is then introduced into this vector previously treated with HindIII and BamHI in order to remove the sequence coding for rHV2Lys47.

The SphI-SalI fragment of M13TG4803 is introduced into the plasmid pTG3828 (see Example 1.B. of the international application) opened at the SphI and SalI sites, to give the vector for the expression of xenoxin-1, which contains:

the sequence of the URA3 gene carrying a deletion of its promoter (URA3-d), the MFα1 gene promoter followed by an ATG, the sequence XII as signal peptide, the mutated "pro" sequence of the MFα1 gene followed by the codons coding for Lys-Arg, the sequence coding for xenoxin-1, the transcription terminator of the gene coding for yeast PGK, a fragment of pBR322 which permits replication and selection in *E. coli,* a fragment of 2 μ plasmid which possesses structural elements needed for replication and for mitotic equipartition in yeast.

An *S. cerevisiae* strain is transformed, which strain is cultured under known conditions.

3.2. Construction of pTG8709 and Analysis of the Mature Xenoxin-1 Secreted into the Culture Medium The sequence coding for mature xenoxin-1, provided with an EagI site at the 5' end and a SalI site at the 3' end, is amplified by PCR. M13TG4414 or pTG4414 (Kolbe et al., J. Biol. Chem., 268, (1993) p.16458) is used as template, and the following primers are used: and The fragment thus generated is integrated in M13TG9800 previously digested with EagI and SalI to give M13TG8703. The vector M13TG9800 originates from M13TG131 into which are inserted the elements essential to the expression of a protein of interest, namely:

The MFα1 gene promoter followed by an ATG codon (Inokuchi et al., Mol. Cell. Biol. 7 (1987) p. 3185)

The BGL2 (β-glucanase 2; Klebl and Tanner, J. Bacteriol., 171 (1989) p. 6259 pre sequence The pro sequence of defensin A (Dimarcq et al., EMBO J. 9 (1990) p. 2507) into which an EagI site has been introduced silently at its 3' end (covering the codons preceding those coding for the Lys-Arg residues at the 3' end).

Restriction sites for the insertion of a DNA sequence of interest.

The SphI-SalI fragment isolated from M13TG8703 and carrying the cassette for the expression of mature xenoxin-1 is introduced between the same sites of pTG4812 to obtain pTG8709. The vector pTG4812 is derived from pTG3828, but comprises, in addition, a cassette for the expression of the yeast KEX2 gene inserted at the junction of the 2 μ portion and the pBR322 portion.

pTG8709 is transformed into a *Saccharomyces cerevisiae* strain. TGY47.1 (MATα, pra1, prb1, prc1, cps1, ura3-delta5, leu2-3, leu 2-112, his) or TGY73.4, which is derived from the latter but displays a prototrophy for leucine ($Leu^+$), may be mentioned as examples.

A transformant TGY73.4/pTG8709 is selected and cultured at 28° C. in minimum selective medium (0.67% of nitrogenous bases for yeast YNB (Yeast Nitrogen Base) without amino acid, 1% of casamino acids, 2% of glucose and 2% of bactoagar).

After 60 hours of culture, the culture supernatant is concentrated by ultrafiltration through a YM2 membrane/centrifugation according to conventional techniques. The concentrate is subjected to denaturing electrophoresis on polyacrylamide gel (15.3% of polyacrylamide). The proteins are transferred onto a PVDF membrane, and the material corresponds [sic] to the expected molecular weight (approximately 7kDa) is subjected to sequencing of the N-terminal amino acids.

A sequence which corresponds to the N-terminal sequence expected for mature xenoxin-1 is read as the predominant component.

What is claimed is:

1. An isolated DNA fragment comprising a sequence coding for a peptide comprising an amino acid sequence which:

a. contains at least 8 cysteines which, when the peptide adopts its folded conformation, are linked through 4 disulfide bridges according to the arrangement $Cys^1$ with $Cys^3$, $Cys^2$ with $Cys^4$, $Cys^5$ with $Cys^6$ and $Cys^7$ with $Cys^8$;

b. contains 0 to 3 amino acids on the N-terminal side of $Cys^1$, 9 to 14 amino acids between $Cys^1$ and $Cys^2$ , 3 to 7 amino acids between $Cys^2$ and $Cys^3$, 11 to 18 amino acids between $Cys^3$ and $Cys^4$, 1 to 6 amino acids between $Cys^4$ and $Cys^5$, 7 to 15 amino acids between $Cys^5$ and $Cys^6$, no amino acid between $Cys^6$ and $Cys^7$, 3 to 5 amino acids between $Cys^7$ and $Cys^8$ and 0 to 10 amino acids on the C-terminal side of $Cys^8$; and c. displays an identity of amino acids, after alignment, of at least 40% with the amino acid sequence identified under the number SEQ ID NO: 3, or a fragment thereof.

2. An isolated DNA fragment comprising a sequence coding for the precursor of a peptide according to claim 1.

3. A DNA fragment according to claim 1, wherein said sequence codes for an amino acid sequence as identified under the number SEQ ID NO:3, SEQ ID NO: 4 or SEQ ID NO: 5.

4. A DNA fragment according to claim 1, wherein said fragment comprises a nucleic acid sequence coding for an amino acid sequence as identified under the number SEQ ID NO: 1 and extending from the base at position 93 to the base at position 290.

5. A DNA fragment according to claim 2, wherein said fragment comprises a nucleic acid sequence coding for an amino acid sequence as defined under the number SEQ ID NO: 1 and extending from the nucleic acid at the position 39 to the nucleic acid at position 290.

6. A cassette for the expression of an isolated DNA fragment according to claim 1, wherein said DNA fragment is placed under the control of elements permitting its transcription or translation in the transformed cell in question.

7. An expression cassette according to claim 6, wherein said cassette further comprises a pre sequence and a pro sequence, in particular the pro sequence of *Phortilia terranovae* defensin A.

8. A cassette for the expression of an isolated DNA fragment according to claim 2, wherein said DNA fragment is placed under the control of elements permitting its transcription or translation in the transformed cell in question.

9. A cell transformed with an expression cassette according to claim 6, wherein said expression cassette is either integrated in the genome of the transformed cell or carried by an expression vector.

10. A transformed cell according to claim 9, characterized in that it is chosen from the group consisting of *S. cerevisiae* and *E. coli.*

11. A transformed cell according to claim 9, characterized in that the cell is of mammalian origin.

12. A pharmaceutical composition for human or veterinary use comprising at least one vector comprising an expression cassette according to claim 6.

13. A pharmaceutical composition for human or veterinary use comprising at least one transformed cell according to claim 9.

14. A monoclonal or polyclonal antibody that recognizes a peptide according to claim 1.

15. A diagnostic kit comprising an antibody according to claim 14.

16. A method for preparing a peptide according to claim 1, wherein a cell transformed with a cassette for the expression of an isolated DNA fragment which comprises a sequence coding for said peptide is cultured on a suitable medium and said peptide is recovered from said culture.

17. The DNA fragment according to claim 1, comprising a sequence coding for a peptide comprising an amino acid sequence which contains 2 amino acids on the N-terminal side of $Cys^1$, 10 to 13 amino acids between $Cys^1$ and $Cys^2$, 4 to 6 amino acids between $Cys^2$ and $Cys^3$, 12 to 17 amino acids between $Cys^3$ and $Cys^4$, 1 to 5 amino acids between $Cys^4$ and $Cys^5$, 8 to 14 amino acids between $Cys^5$ and $Cys^6$, no amino acids between $Cys^6$ and $Cys^7$, 4 amino acids between $Cys^7$ and $Cys^8$, and 2 amino acids on the C-terminal side of $Cys^8$.

18. The DNA fragment according to claim 1, comprising a sequence coding for a peptide, wherein said amino acid sequence of said peptide displays an identity of amino acids of at least 50% with the sequence of amino acids identified under the number SEQ ID NO:3.

19. The DNA fragment according to claim 18, wherein the identity of amino acids is at least 70%.

20. The DNA fragment according to claim 1, comprising a sequence coding for a peptide comprising an amino acid sequence which contains 0 to 3 amino acids on the N-terminal side of $Cys^1$, 13 amino acids between $Cys^1$ and $Cys^2$, 6 amino acids between $Cys^2$ and $Cys^3$, 12 amino acids between $Cys^3$ and $Cys^4$, 5 amino acids between $Cys^4$ and $Cys^5$, 14 amino acids between $Cys^1$ and $Cys^6$, no amino acids between $Cys^6$ and $Cys^7$, 4 amino acids between $Cys^7$ and $Cys^8$, and 0 to 10 amino acids on the C-terminal side of $Cys^8$, and which displays an identity of amino acids, after alignment, of at least 80% with the sequence of amino acids identified under the number SEQ ID NO:3.

21. The DNA fragment according to claim 20, wherein the identity of amino acids is at least 95% with the sequence of amino acids identified under the number SEQ ID NO:3.

* * * * *